United States Patent [19]
Jiang et al.

[11] Patent Number: 5,480,961
[45] Date of Patent: Jan. 2, 1996

[54] BIOABSORBABLE POLYMERS DERIVED FROM CYCLIC ETHER ESTERS AND SURGICAL ARTICLES MADE THEREFROM

[75] Inventors: Ying Jiang, North Haven; John S. Bobo, Guilford, both of Conn.

[73] Assignee: United States Surgical Corporation, Norwalk, Conn.

[21] Appl. No.: 333,807

[22] Filed: Nov. 3, 1994

[51] Int. Cl.$^6$ .................................................. C08G 8/02
[52] U.S. Cl. ........................... 528/220; 524/777; 524/779; 524/785; 528/228; 606/228; 606/230; 606/232
[58] Field of Search ............................... 524/77, 779, 785; 528/220, 222; 606/230, 232, 228

[56] References Cited

U.S. PATENT DOCUMENTS

| | | | |
|---|---|---|---|
| 3,562,295 | 2/1971 | Pedersen. | |
| 3,860,611 | 1/1975 | Krespan | 549/351 |
| 3,928,386 | 12/1975 | Dale et al. | 549/352 |
| 4,140,847 | 10/1979 | Orvik et al. | 528/403 |
| 4,243,775 | 1/1981 | Rosensaft et al. | 525/415 |
| 4,256,859 | 3/1981 | Woo | 525/333.4 |
| 4,297,102 | 10/1981 | Vanlerberghe et al. | 8/406 |
| 4,328,168 | 5/1982 | Fayter, Jr. | 558/366 |
| 4,436,923 | 3/1984 | Pacey et al. | 549/352 |
| 4,474,963 | 10/1984 | Gokel | 546/178 |
| 4,504,368 | 3/1985 | Delton et al. | 204/153.15 |
| 4,523,994 | 6/1985 | Shono et al. | 210/500.28 |
| 4,570,004 | 2/1986 | Lagow et al. | 549/352 |
| 4,631,119 | 12/1986 | Gokel et al. | 204/59 R |
| 4,900,845 | 2/1990 | Brisdon et al. | 549/352 |
| 4,959,069 | 9/1990 | Brennan et al. | 606/228 |
| 5,019,093 | 5/1991 | Kaplan et al. | 606/228 |
| 5,037,429 | 8/1991 | Hermes et al. | 606/230 |
| 5,047,563 | 9/1991 | Denton et al. | 549/353 |
| 5,051,272 | 9/1991 | Hermes et al. | 604/304 |
| 5,059,213 | 10/1991 | Chesterfield et al. | 606/228 |
| 5,076,807 | 12/1991 | Bezwada et al. | 606/230 |
| 5,080,665 | 1/1992 | Jarrett et al. | 606/219 |
| 5,106,995 | 4/1992 | Plotkin | 549/273 |
| 5,132,436 | 7/1992 | Engebrecht et al. | 549/353 |
| 5,312,642 | 5/1994 | Chesterfield et al. | 427/231 |

OTHER PUBLICATIONS

Encyclopedia of Chemical Technology, 3rd Edition, vol. 18 pp. 252 and 267–270 (1982).
Encyclopedia of Chemical Technology, 3rd Edition, vol. 9 pp. 384–436 (1982).

*Primary Examiner*—Shelley A. Dodson

[57] ABSTRACT

Bioabsorbable polymers are obtained from the polymerization of cyclic ether-esters which are derived from crown ethers. The bioabsorbable polymers are useful in forming surgical articles including sutures and suture coating compositions.

7 Claims, 1 Drawing Sheet

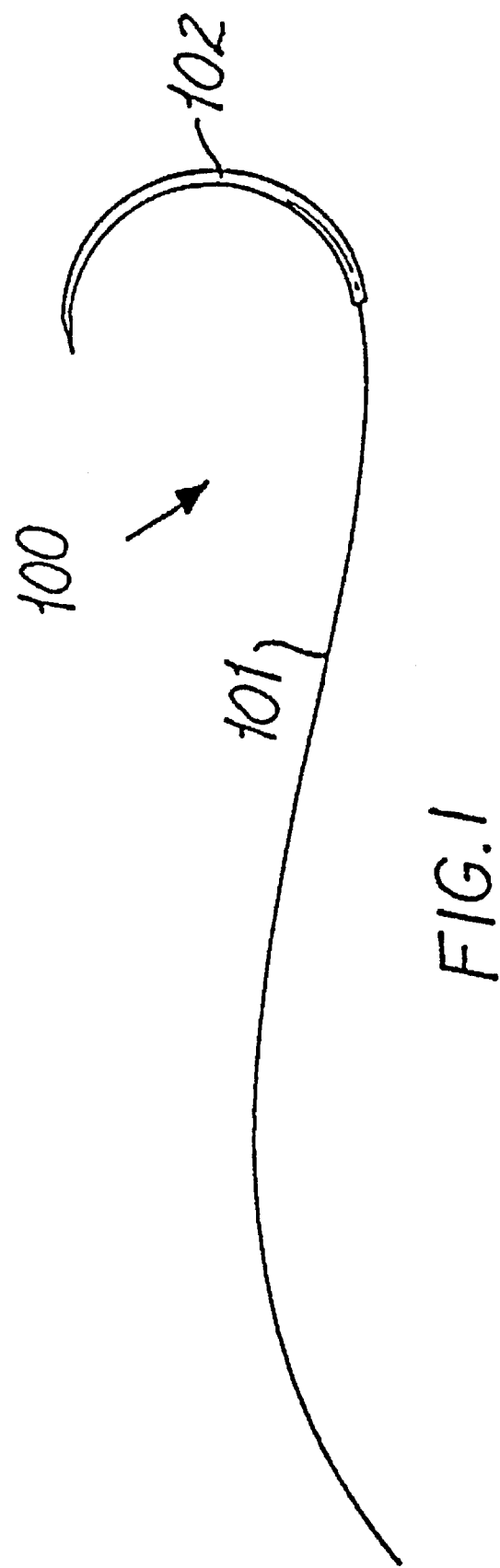

BIOABSORBABLE POLYMERS DERIVED FROM CYCLIC ETHER ESTERS AND SURGICAL ARTICLES MADE THEREFROM

BACKGROUND

1. Technical Field

Bioabsorbable polymers made from cyclic ether-esters derived from crown ethers are described herein. Surgical articles prepared from such polymers are also disclosed.

2. Background of Related Art

Crown ethers or macrocyclic ethers generally comprise repeating ethyleneoxy (—O—$CH_2$—$CH_2$—) units. These macrocyclic polyethers are commonly known as crown ethers because their molecular models resemble crowns. Crown ethers are designated N-crown -M polyethers wherein N is the total number of atoms and M is the number of oxygen atoms in the polyether ring. Crown ethers are well known ion complexing compounds which are used as phase transfer catalysts in many organic reactions. Crown ethers are used in a variety of applications. For example, U.S. Pat. No. 3,860,611 discloses polyols containing macrocyclic polyether rings. Hydrolysis of the macrocyclic polyethers yields diols which are condensed with diacids or diisocyanates to form polyesters or polyurethanes which complex with metal salts.

U.S. Pat. No. 4,328,168 discloses vinylcyclopropane derivatives reacted to obtain monomers useful for the preparation of oligomers which may be further polymerized by light, organic peroxides, or other means. Cyclic polyether compounds are employed as catalysts to obtain the vinylcyclopropane derivatives.

U.S. Pat. No. 4,570,004 discloses perfluorinated crown ethers useful as oxygen carriers and for other biomedical purposes, such as the coordination of toxic metals in the blood stream.

Bioabsorbable polymers and copolymers having glycolic acid ester linkages and/or dioxanone linkages are well-known. See, e.g., U.S. Pat. Nos. 4,243,775, 4,643,191, 5,076,807, 5,080,665, and 5,100,433.

The present disclosure provides a process for preparing bioabsorbable polymers derived from cyclic ether-esters synthesized from crown ethers. As the ester functional group is introduced into the cyclic monomer, the ester and ether linkage and their sequences in the final polymers can be easily controlled and modified to obtain polymeric materials with desirable physical and degradation properties for a variety of applications.

SUMMARY

In accordance with this disclosure, crown ethers are oxidized to form cyclic ether-esters. Bioabsorbable polymers are obtained by ring-opening polymerization of the cyclic ether-esters. The polymers described herein are useful in forming surgical articles, including sutures, both monofilament and multifilament, as well as suture coatings.

BRIEF DESCRIPTION OF THE DRAWINGS

FIG. 1 is a depiction of a needled suture in accordance with the present disclosure.

DETAILED DESCRIPTION OF PREFERRED EMBODIMENTS

The bioabsorbable polymers described herein are made by oxidizing a crown ether to prepare a cyclic ether-ester and then polymerizing the cyclic ether-ester. Thus, polymers made in accordance with this disclosure have glycolic acid ester-like linkages or dioxanone-like linkages derived from the ring-opening polymerization of the cyclic ether-esters. They are particularly useful as surgical articles because they are bioabsorbable. That is to say, the polymers are capable of degradation and elimination from a body without adverse side effects.

The crown ethers or cyclic polyethers employed herein may be obtained by methods that are well known in the art. Crown ethers are obtained by Williamson ether synthesis which involves nucleophilic substitution of an alkyl halide by an alkoxide ion. A linear polyether having halide and alkoxide functions at opposite ends is used to prepare the crown ether. Alternatively, two linear polyethers which are terminally substituted so that one polyether has a halide function and the other an alkoxide function may be used to obtain the crown ether. See U.S. Pat. No. 3,562,295 hereby incorporated by reference.

Crown ethers may also be prepared from ethylene oxide in the presence of fluorinated Lewis acids such as boron trifluoride, phosphorous pentafluoride, or antimony pentafluoride. See the Encyclopedia of Chemical Technology, 3rd Edition, Volume 9, pp. 384 and 436. See also U.S. Pat. Nos. 3,928,386 and 4,256,859. All of the foregoing documents are hereby incorporated by reference. Certain crown ethers such as, for example, 18-crown-6, are commercially available from Aldrich Chemicals, Milwaukee, Wis.

The crown ethers have the following structure:

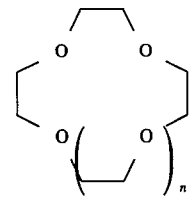

wherein n is at least 1, preferably n is 1 to 12, and most preferably 1 to 3. A particularly preferred crown ether is 12-crown-4 ether a cyclic tetramer of ethylene oxide.

The crown ethers are oxidized to produce cyclic ether-esters. Any method may be employed to oxidize the crown ether. For example, the crown ether may be reacted with an oxidizing agent. A preferred oxidizing agent is ruthenium tetroxide ($RuO_4$). Ruthenium tetroxide is produced upon interaction of alkaline ruthenium salts with chlorine or bromate. Ruthenium tetroxide is capable of acting as a stoichiometric oxidant for converting ethers to esters or lactones. Furthermore, ruthenium can also be used in catalytic amounts to convert ethers to esters where the ruthenium is in the form of ruthenium trichloride or ruthenium oxide in the presence of an oxidant such as sodium hypochlorite. Other suitable oxidants are calcium hypochlorite, chromium trioxide in sulfuric acid, and sodium periodate. A suitable solvent for ruthenium tetroxide is carbon tetrachloride. Other suitable solvents are those which are resistant to oxidation by the oxidizing agent, for example, water, ethyl acetate, benzyltriethyl ammonium permanganate, acetonitrile, dimethylformamide and the like. See U.S. Pat. No. 5,106,995 and the Encyclopedia of Chemical Technology, 3rd Edition, Volume 18, pp. 252 and 267–270 (1982), the disclosures of which are incorporated herein by reference.

The precise reaction conditions employed for the oxidation of the crown ethers will depend on a number of factors including, for example, the particular starting materials and the desired degree of oxidation to be achieved.

A solution of oxidizing agent in a suitable solvent is formed. The solution should contain from 0.1 to 1 mole of oxidizing agent per liter of solution. The crown ether is slowly added to the solution with stirring at a temperature ranging from about 0° to about 30° C. The crown ether may itself be dissolved in a suitable solvent to facilitate addition and mixing of the crown ether. The ratio of oxidizing agent to crown ether oxygen number during the oxidizing reaction can range from about 0.001:1 to about 10:1 with 0:1 to 4:1 being preferred, and 1:1 to 2:1 being the most preferred for preparing the cyclic ether-esters. This reaction is allowed to proceed for about 60 minutes to 24 hours or longer.

Without being limited to any particular structures, the resulting structure of the cyclic ether-ester is determined by the molar ratio of the oxidizing agent to the crown ether. Furthermore, the structure of the bioabsorbable polymer is determined by the formula of the ring-opened cyclic ether-ester monomeric units. The general formula of the present cyclic ether-esters is the following:

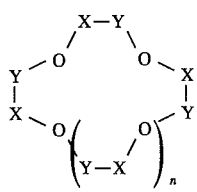

wherein each X is the same or different and individually selected from the group consisting of —CH$_2$—, —CHR$_1$— and —CR$_2$R$_3$—; R$_1$, R$_2$ and R$_3$ are individually selected from alkyl groups having from 1 to 3 carbons; each Y is the same or different and is individually selected from the group consisting of X and

provided that at least two of the Y's are

and n is at least 1.

In a particularly useful embodiment, total oxidation of the crown ethers produces cyclic polyesters wherein all Y's of the crown ether are

The cyclic polyester monomers are polymerized to form bioabsorbable polymers. Total oxidation of the crown ethers can be achieved by employing an excess amount of oxidizing reagent. For example, ruthenium tetroxide may be used as the oxidizing agent in a 1:1 to 1.2:1 ratio with the crown ether oxygen number. In a particularly useful embodiment, a ratio of oxidizing agent to crown ether oxygen number of 1.2:1 is employed.

Other bioabsorbable polymers are obtained in accordance with the methods described herein from the oxidation of crown ethers wherein the oxidizing agent, such as ruthenium tetroxide, is present in a molar ratio with the crown ether which does not result in total oxidation. A 1:2 ratio of ruthenium tetroxide to crown ether oxygen number produces a cyclic ether-ester of the following formula:

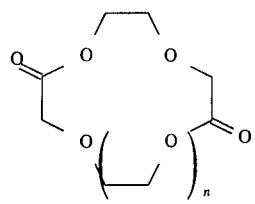

Ratios of ruthenium tetroxide to crown ether oxygen number intermediate 1.2:1 and 1:2 will produce cyclic ether-esters having an intermediate amount of conversion to ester groups.

The bioabsorbable polymers described herein are obtained by ring-opening polymerization of cyclic ether-esters in the presence of an organometallic catalyst A preferred catalyst for use is stannous octoate. Other suitable catalysts include Lewis acids such as aluminum chloride and zinc chloride and the like. However, the present disclosure is not limited to those compounds.

The polymerization of cyclic monomers is influenced by the ring size, reactivity characteristics of functional groups, and substituents on the ring. Ring-opening polymerizations can proceed through a wide variety of mechanisms depending on the monomers and catalysts employed. See the Encyclopedia of Polymer Science and Engineering, Volume 14, pp. 622–647 (1989), the disclosure of which is incorporated herein by reference. It is within the purview of those skilled in the art to determine the appropriate polymerization parameters to provide polymers having the desired characteristics in view of the disclosure herein.

In a preferred polymerization procedure, cyclic ether-ester is heated under nitrogen at a temperature ranging from 100° C. to 250° C., preferably above 110° C. for 24 hours. In a typical experiment, 50 grams of the cyclic ether-ester are placed in a polymerization tube. Then about 0.02% by weight of stannous octoate is added to the tube and dried under vacuum for 6 hours. 0.02% by weight of stannous octoate is preferred. Polymerization is conducted under a nitrogen atmosphere at a temperature from about 100° C. to about 250° C. The polymerization time may range from 12 to 48 hours depending on the other polymerization parameters, but generally polymerization times of 24 hours are employed. The resulting polymers are extruded and treated (with heat, either under vacuum or a flow of dry inert gas) to remove unreacted residual monomer or other volatile impurities using methods well known in the art.

The bioabsorbable polymers herein can be used in the fabrication in whole or in part of a variety of surgical articles. These include, but are not limited to sutures, suture coatings, pins, screws, clips and other fasteners, gauze, wound dressings, hernial repair meshes, anastomosis rings, prosthetic ligaments and tendons, growth matrices, drug delivery devices and other implantable medical devices.

Drug delivery devices, as used herein, include any drive or article of manufacture which is used to deliver a medicinal agent. The term "medicinal agent" is used in its broadest sense and includes any substance or mixture of substances which is useful in medicine. Thus, it is understood that a medicinal agent may be a drug, enzyme, growth factor, peptide, protein, dye or diagnostic agent such as a releasable dye which may have no biological activity per se.

Examples of various medicinals that can be used in accordance with this disclosure include antimicrobials, analgesics, antipyretics, anesthetics, antiepileptics, antihistamines, antiinflammatories, cardiovascular drugs, diagnostic agents, sympathomimetics, cholinomimetics, antimuscarinics, antispasmodics, hormones, growth factors, muscle relaxants, adrenergic neuron blockers, anti-neoplastics, immunosuppressants, gastrointestinal drugs, diuretics, steroids and enzymes. It is also intended that combinations of medicinals can be used in accordance with the present disclosure.

The polymers herein may be formed into surgical articles using any known technique, such as, extrusion, molding and/or solvent casting. The polymers may be spun into fibers to be used as sutures, either monofilament or multifilament, or are woven with other fibers, either absorbable or nonabsorbable, to form meshes or fabrics.

Monofilament sutures can be manufactured from the polymer by methods that are well known in the art. A suitable process for the manufacture of a monofilament suture comprises the operations of melt extruding the polymer herein to provide a monofilament, stretching the solidified monofilament at an elevated temperature in water (or other suitable liquid medium) or in air (or other suitable gaseous medium) to provide a stretched monofilament. Optionally, the monofilament can be annealed to provide a finished suture.

Multifilament sutures can be made by methods that are well known in the art. Braid construction such as those disclosed in U.S. Pat. Nos. 4,959,069, 5,019,093 and 5,059,213 are suitable for the construction of multifilament sutures. Multifilament sutures can be coated or filled with substances which improve their functional characteristics, e.g., their lubricity, knot tie-down properties, knot security properties, etc.

It is contemplated that it may be desirable to dye the suture in order to increase its visibility in the surgical field. Dyes known to be suitable for incorporation in sutures can be used. Such dyes include, but are not limited to, logwood extract, carbon black and D & C Green No. 6 as described in "U.S. Colorants for Food, Drugs, and Cosmetics", by Daniel M. Matron (1979). Preferably, a suture in accordance with this disclosure is dyed by incorporating up to about a few weight percent of a dye such as D & C Green No. 6 into the polymer prior to extrusion.

Surgical articles made from the polymers described herein can be used to secure tissue in a desired position. A wound closure device 100 in accordance with the present disclosure, may include a suture 101 attached to a surgical needle 102 as shown in FIG. 1. Wound closure can be achieved by approximating tissue and by passing the needled suture through tissue to create wound closure. The needle preferably is then removed from the suture and the suture tied.

In another embodiment, suture coatings comprising the bioabsorbable polymers herein can be applied to sutures by any suitable process, such as, for example, passing the suture through a solution of polymer, e.g., in acetone, methylene chloride, etc. The polymer can also be applied to the suture by a brush or other coating solution applicator or by spray nozzles which dispense the suture coating solution. After the suture is wetted with the coating solution, it is subsequently passed through or held in a drying oven for a time and at a temperature sufficient to vaporize and drive off the solvent. If desired, the suture coating composition can optionally contain additional components, e.g., dyes, antibiotics, antiseptics, growth factors, and anti-inflammatory agents.

The coating composition herein can be applied to any type of suture. A preferred type of suture is a braided suture which is disclosed in U.S. Pat. No. 5,019,093, the contents of which are incorporated by reference herein. The amount of coating composition applied to a braided suture will vary depending upon the structure of the suture, e.g., the number of filaments, tightness of braid or twist, the size of the suture and its composition.

The coating composition herein can be used for both "unfilled" as well as "filled" sutures, the latter designating braided bioabsorbable sutures containing a storage stabilizing material as disclosed in U.S. Pat. Nos. 5,037,429 or 5,051,272, the contents of which are incorporated by reference herein. For an "unfilled" suture, the coating composition can be applied at a level of from about 0.5 to about 4 weight percent or more and preferably from about 1 to about 3 weight percent. Advantageously, the coating composition is applied to the suture prior to application of the storage stabilizing material. For a filled suture, the amount of applied coating composition can range from about 0.2 to as much as about 3 weight percent or more and preferably from about 0.5 to about 2 weight percent As a practical matter, it is generally preferred to apply the minimum amount of coating composition consistent with good tie-down performance. This level of coating add-on can be readily determined for any particular suture coating system employing routine experimental procedures.

In the case of an unfilled or filled braided suture, prior to application of the coating composition, it can be advantageous to calendar the suture in order to improve the uniformity with which the coating composition is laid down upon the suture surface. A calendering operation can also be beneficial when carried out on a coated suture where the suture is to be filled with a storage stabilizing material. In this case, calendering will tend to break up the coating facilitating penetration of the interior spaces of the suture by the storage stabilizing material.

A preferred method for calendering a braided suture and an apparatus for carrying out the method are disclosed in U.S. Pat. No. 5,312,642, the contents of which are incorporated by reference herein.

The following examples are illustrative of the bioabsorbable polymers of the disclosure and surgical articles made therefrom.

EXAMPLE 1

Preparation of the Cyclic Ether-ester 17.6 grams of 12-crown-4 are mixed in 200 ml of carbon tetrachloride. The mixture is cooled to 0° C., and then, a solution of ruthenium oxide (13.4 grams) and sodium periodate (21.4 grams) in 400 ml of carbon tetrachloride is added at 0° C. and is stirred for 30 minutes. Vigorous stirring is continued for an additional 60 minutes at 0° C., then the reaction temperature is slowly raised to room temperature. Insoluble materials are removed by filtration and the solvent removed in vacuo to obtain the product.

EXAMPLE 2

Ring-opening Polymerization of Cyclic Ether-esters 5 grams of the cyclic ether ester prepared in accordance with Example 1 are placed in a polymerization tube and 1 milligram of stannous octoate is added. The mixture is dried under vacuum for 6 hours at room temperature. The tube is then sealed and heated at 125° C. for 24 hours. The product is obtained by breaking the tube.

EXAMPLE 3

Procedure for Coating Sutures With the Bioabsorbable Polymers 2 grams of the material prepared in Example 2 is dissolved in 10 grams of methylene chloride at room temperature to form a coating solution. Absorbable sutures are then dip-coated in the solution. The coating is applied at a level of 1 to 3 weight percent of the entire coated suture. The coated sutures show improved surface properties.

It will be understood that various modifications may be made to the embodiments disclosed herein. For example, the compositions in accordance with this disclosure can be blended with other biocompatible, bioabsorbable or non-bioabsorbable materials. Therefore, the above description should not be construed as limiting, but merely as an exemplification of preferred embodiments. Those skilled in the art will envision other modifications within the scope and spirit of the claims appended hereto.

What is claimed is:

1. A bioabsorbable polymer derived from at least one type of cyclic ether-ester monomeric unit of the formula:

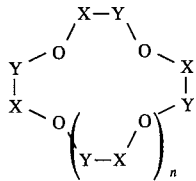

wherein each X is the same or different and individually selected from the group consisting of $CH_2-$, $-CHR_1-$ and $-CR_2R_3-$ wherein $R_1, R_2$ and $R_3$ are individually selected from alkyl groups having from 1 to 3 carbons;

each Y is the same or different and is individually selected from the group consisting of
X and

provided that at least two of the Y's are

and
n is at least 1.

2. The bioabsorbable polymer according to claim 1, wherein said cyclic ether-ester monomer comprises at least one type of monomer of the formulas I and II:

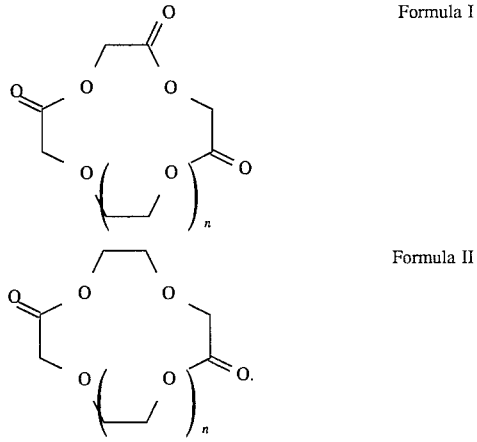

3. The bioabsorbable polymer according to claim 1, wherein all of the Y's of said cyclic ester monomeric unit comprise

4. A surgical article fabricated from the bioabsorbable polymer of claim 1.

5. The surgical article of claim 4, which is selected from the group consisting of a suture, staple, pin, screw, clip, wound dressing and drug delivery device.

6. The surgical article of claim 5, further comprising a coating of the bioabsorbable polymer on a suture.

7. The suture article of claim 6, wherein the coating composition is applied to a suture at a level from about 0.2 to about 4 weight percent of the entire coated suture.

* * * * *